United States Patent [19]

Burke et al.

[11] Patent Number: 4,835,149

[45] Date of Patent: May 30, 1989

[54] SOLUBILIZATION OF SALTS OF PYRIDINE-2-THIOL-1-OXIDE

[75] Inventors: John J. Burke, Farmington Hills; Robert R. Roelofs, Lincoln Park; Michael G. Kinnaird, Southgate, all of Mich.

[73] Assignee: BASF Corporation, Parsippany, N.J.

[21] Appl. No.: 930,009

[22] Filed: Nov. 13, 1986

[51] Int. Cl.$^4$ .............................................. A61K 31/555
[52] U.S. Cl. .................................. 514/188; 514/852; 514/864
[58] Field of Search ....................... 514/188, 852, 864

[56] References Cited

U.S. PATENT DOCUMENTS

| | | | |
|---|---|---|---|
| 3,636,213 | 1/1972 | Gerstein et al. | 514/852 |
| 3,785,985 | 1/1974 | Grand | 514/188 |
| 3,940,482 | 2/1976 | Grand | 514/188 |
| 4,235,898 | 11/1980 | Watanabe et al. | 514/852 |
| 4,379,753 | 4/1983 | Bolich, Jr. | 514/188 |

FOREIGN PATENT DOCUMENTS

| | | | |
|---|---|---|---|
| 77630 | 4/1983 | European Pat. Off. | 514/188 |
| 0200305 | 11/1986 | European Pat. Off. | |
| 1202716 | 8/1970 | United Kingdom | |

OTHER PUBLICATIONS

Gerstein, Journal of the Society of Cosmetic Chemists 23, 99–114, 1972.

Akamura et al., Chemical Abstracts, vol. 85, No. 18, Nov. 1, 1977, p. 444, Abstract No. 130370M.

Primary Examiner—Allen J. Robinson
Attorney, Agent, or Firm—Bill C. Panagos

[57] ABSTRACT

A composition of matter comprising a metal pyrethione salt, an amine having the following formula

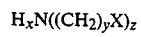

wherein x is 0 to 2, y is 1 to 3, z is 1 to 3, x+z=3 and X is H, OH or COOH and an aminocarboxylic acid selected from the group consisting of ethylenediaminetetraaceteic acid, diethylenetriaminepentaacetic acid, nitrilotriacetic acid, N(hydroxide ethyl) ethylenediaminetriacetic acid, cyclohexanediamine tetracetic acid, triethanolamine ethylenediamine tetracetic acid and acids having the formulas:

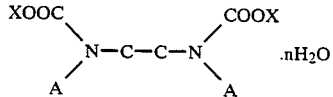

where X is H, lithium, sodium, potassium, cesium, magnesium, calcium, nickel, copper, zinc and mixtures thereof. A is H or COOX and n is an integer or zero.

6 Claims, No Drawings

SOLUBILIZATION OF SALTS OF PYRIDINE-2-THIOL-1-OXIDE

BACKGROUND OF THE INVENTION

The present invention relates to methods of solubilizing metal salts of pyridine-2-thiol-1-oxide, to such solubilized salts, and to compositions containing the solubilized salts. Such products are particularly useful as microbiocides in the cosmetic, pharmaceutical and textile treatment arts.

Metal salts of pyridine-2-thiol-1-oxide (often referred to as "pyrithione") are described in detail in U.S. Pat. No. 2,809,971. As there discussed, the metal salts are conveniently prepared by reaction of a soluble metal compound with a soluble salt of pyrithione, such as an alkali metal salt or ammonium salt. On combination of these reactants, the metal salt precipitates and is recovered. Metal salts in the present specification particularly include salts like those disclosed in said U.S. Pat. No. 2,809,971, i.e., salts in which the metal group is inter alia, copper, iron, manganese, tin, mercury, cobalt, chromium, lead, gold, cadmium, nickel, silver, zinc, titanium, arsenic, antimony, zirconium, or bismuth. As in the aforementioned patent, the term "metal" as employed in the present specification includes elements of metallic character such as arsenic, characterized in the patent as "semi-metals" and also ammonium salts.

The salts of pyrithione are useful as fungicides and bactericides, and certain of them are particularly adaptable to topical application to the skin. The zinc salt specifically is quite effective as an agent against seborrhea, and has found wide acceptance in the cosmetic art for use in soaps, shampoos, hairdressings, and the like.

One disadvantage of the metal salts of pyrithione, such as the zinc salt, is their insolubility in common solvents. The zinc salt, for example, is substantially insoluble in water (10-20 p.p.m.), ethanol (310 p.p.m.) benzene (3-5 p.p.m.), petroleum oils, and most common organic solvents. The material is slightly more soluble in chloroform (3400 p.p.m.), dimethyl formamide (8100 p.p.m.) and dimethyl sulfoxide (5.13 percent). Accordingly, it has been found difficult to formulate suitable cosmetic and other compositions containing these heavy metal salts in dissolved form. The few solvents known for the salts are unacceptable for cosmetic uses and the salts must always be present in such compositions in dispersed form, necessarily rendering the compositions opaque. Although there are soluble salts or pyrithione, such as the alkali metal salts, these soluble salts are thought to be toxic and unacceptable for use at active levels in cosmetic or dermatologic compositions for topical application to the skin.

U.S. Pat. No. 3,636,213 discloses the solubilization of metal salts of pyrithione in common organic solvents and/or water by combination with an amine and also including an aqueous or ethanolic solution of an acid, generally a physiologically acceptable acid. The patent discloses compositions having pH's of from about 8.5 to 9.0.

U.S. Pat. Nos. 3,940,482 and 3,785,985 as well as the article "Clear Zinc Pyrithione Preparations" by T. Gerstein in the *Journal of the Society of Cosmetic Chemistry*, vol 23, p. 99-114 (Feb 1972) all disclose solubilization of metal pyrithiones by combination with an amine.

It is known that heavy metal pyrithione solubility is increased in an alkaline media. For example, the zinc salt is soluble in water at pH 7 to an extent of about 10 to 20 parts per million. This is raised to a value of 35 to 50 parts per million at a pH of 8. U.S. Pat. No. 3,636,213 teaches that the solubility of the zinc salt according to that invention, in a composition having a pH of about 8, can be as high as at least 200 parts per million or higher.

Current state of the art limits the practical use of soluble salts of pyridine-2-thiol-1-oxide in aqueous systems to a pH of about 8.5 and higher. This dramatically hampers the use of such salts in the art of designing modern hair- and skin-applied products. Those skilled in such cosmetic and pharmaceutical arts readily acknowledge the importance of maintaining a product pH matched closely to that of the intended substrate, namely, the skin. Skin is a biological organ and its character may, therefore, vary extensively from person to person. Its pH may also vary as well although its range is generally recognized as 4.0 to 7.5. The acidic environment has several advantages but perhaps the primary function is the control of harmful microbes on the surface to avoid infection. The topical application of a hair or skin care product that inherently has an alkaline character may, among other things, cause a disruption of this "acid mantle" of the skin thereby potentially compromising its function.

Accordingly it is a purpose of the instant invention to provide a solubilized pyrithione salt for cosmetic applications such as hair and skin treating compositions which have a pH between about 4.0 and 7.4.

SUMMARY OF THE INVENTION

It has been found according to the present invention that the insoluble metal salts of pyrithione can be solubilized in common organic solvents and/or water by combination with an amine having the following formula

where x is from 0 to about 2, y is from about 1 to 3, z is about 1 to 3, x+z=3, and X is H, OH or COOH and certain amino carboxylic acids.

The addition of alcohol allows for the solubilization of the pyrithione salts using less aliphatic amine and aminocarboxylic acid.

The above composition is useful at a pH of about 4.0 to 7.4, particularly as an antibacterial agent in various cosmetic compositions such as for use on the hair and skin.

DETAILED DESCRIPTION

Suitable amines for solubilizing the metal pyrithiones which amines are embraced by the above formula include ethanolamine, diethanolamine, diglycolamine, triethanolamine, diethylamine, triethylamine, monoisopropylamine, diisopropylamine, triisopropylamine, and n-propylamines.

The amino carboxylic acids that may be employed in the instant invention are ethylenediaminetetraacetic acid (EDTA), diethylenetriaminepentaacetic acid (DTPA), nitrilotriacetic acid (NTA), N-(hydroxyethyl)ethylenediaminetriacetic acid (HEDTA), cyclohexanediaminetetraacetic acid (CHDTA), triethanolamineethylenediaminetetraacetic acid (TEA-EDTA), and any similar acid having the following formula:

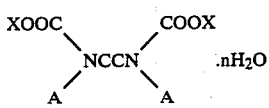

where X equals H, lithium, sodium, potassium, cesium, magnesium, calcium, nickel, copper, zinc or mixtures thereof, A is H or COOX, n is an integer or 0.

Suitable metal salts that may be solubilized in accordance with the instant invention include those listed above with reference to U.S. Pat. No. 2,809,971 and particularly cadmium, zinc, sodium and ammonium salts. While as previously stated alkaline metal salts are generally unacceptable for use in cosmetic or dermatologic compositions for topical application to the skin due to suspected toxicity, they do have other uses.

Alcohols which allow the solubilization of the pyrithione salts using less aliphatic amine and polycarboxylic acid include methanol, ethanol, isopropanol, butanol, propanol, diols and triols having an aliphatic chain length of 2 to 4 carbon atoms, with those units repeating two to three times, ethylene oxide/propylene oxide block copolymers of molecular weight less than 1000, homopolymers of ethylene oxide or propylene oxide of molecular weight less than 1000, thiodiglycol, hexahydric alcohols (sorbitol, mannitol, etc.), disaccharides (sucrose, maltose, etc.) alkylphenol ethoxylates, and other alcohol ethoxylates.

The solubilized heavy metal pyrithione composition contains in percent of the total weight of the composition about 0.1 to 20 percent metal pyrithione; about 0.1 to 60 percent amine of the formula set forth above; about 0.5 to 20 percent aminocarboxylic acid and 0 to about 85 preferably 1.0 to 85 percent diluent which may be water, a conventional solvent or mixture thereof. Where the alcohol is employed, it should be about 0.1 to 70 percent of the compositon, and the ratio of alcohol to amine is about 2:1 to 1:1.

In some cases the amino carboxylic acid itself may be difficultly soluble, and it has been found that a small amount of ammonium hydroxide when included in the composition improves the solubility thereof. Accordingly such compositions may contain from about 0.1 to 20 percent of the ammonium hydroxide based on the total weight including the other 3 to 4 ingredients as the case may be. Also, the ratio of aminocarboxylic acid to ammonium hydroxide is about 3:1 to 1:1.

In addition to the above the ratio of the metal pyrithione salt to the amine of the formula set forth above should be about 1:3 to 1:1.

In one method of preparation the pyrithione is combined with the amine and alcohol (if desired) and mixed to clarity. The polycarboxylic acid is then combined with some of the water and the ammonium hydroxide (if any), and the resulting mixture is slowly added to the pyrithione mix to completion. This soluble composition can then be added to the diluent.

In addition to the above recited components, a typical cosmetic composition could contain a surfactant which may be nonionic, anionic, amphoteric, ampholytic or cationic. Suitable surfactants would include ammonium lauryl sulfate, ammonium lauryl ether sulfate and blends thereof up to about 30 percent active concentration in water. Where employed, the minimum would be about 10 percent. Also other conventional alkyl sulfates and alkyl ethoxysulfates would also be suitable as with anionic sulfonated detergents, acyl sarcosinates and taurates. Nonionic detergents would include ethoxylated alkyl phenols polyoxyethylene/polyoxypropylene block copolymers such as thoses disclosed in U.S. Pat. Nos. 2,674,619; 2,677,700; 3,036,118 and 2,979,528 and sorbitan esters.

The cosmetic compositions may also contain conventional ingredients used in cosmetic and pharmaceutical formulations in amount of from 0 to about 30 percent, preferably about 0.1 to 30 percent. For example these compositions may include as additives antiperspirants and deodorants, e.g., simple deodorants based on oxyquinoline salts, zinc oxide, etc. Astringents such as ammonium chlorohydrates may be included in the cosmetic and pharmaceutical compositions. Such compositions may include shampoos and rich skin creams and as additives may include lanolin, ethoxylated lanolin and mineral oil. In addition the additives may also include antioxidants, essential oils, perfumes and coloring agents.

The following examples illustrate typical compositions according to the invention. As used throughout this specification and claims all parts, proportions and percentages are by weight and all temperatures are in degrees centigrade unless otherwise specified.

Example 1

This example illustrates a shampoo composition including a solubilized salts of pyrithione according to this invention.

| | |
|---|---|
| Ammonium lauryl sulfate/ammonium lauryl ether sulfate blend (28% active) | 70.0% |
| Zinc pyrithione | 1.0 |
| Ethanolamine | 1.4 |
| Diethylene glycol | 2.5 |
| EDTA (ethylenediamine tetra acetic acid) | 7.8 |
| Ammonium hydroxide | 3.2 |
| Water | 14.1 |

The pH was 6.7 and the zinc pyrithione was successfully solubilized.

Example 2

This example illustrates a shampoo composition of the invention where an alcohol is not included:

| | |
|---|---|
| Ammonium lauryl sulfate/ammonium lauryl ether sulfate blend (28% active) | 45.0% |
| Zinc pyrithione | 1.0 |
| Ethanolamine | 4.0 |
| EDTA | 20.0 |
| Ammonium hydroxide | 10.0 |
| Water | 20.0 |

The resulting pH was 7.5; HCL was added to lower the pH further to 6.7. The zinc pyrithione was successfully solubilized.

Example 3

A combination of the use of alcohol and physiologically acceptable acid will achieve a lower pH. An example is:

| | |
|---|---|
| Ammonium lauryl sulfate/ammonium lauryl ether sulfate blend | 70.0% |

| -continued | |
|---|---|
| (28% active) | |
| Zinc pyrithione | 1.0 |
| Ethanolamine | 1.4 |
| Diethylene glycol | 2.5 |
| EDTA | 8.1 |
| Ammonium hydroxide | 4.9 |
| Water | 12.1 |

The resulting pH was 6.46 and the zinc pyrithione was successfully solubilized.

Example 4

This is an example of the use of a different alcohol to achieve the same end result.

| Ammonium lauryl sulfate/ammonium lauryl ether sulfate blend (28% active) | 70.0 |
|---|---|
| Zinc pyrithione | 1.0 |
| Ethanolamine | 1.0 |
| Polyethylene glycol | 2.0 |
| EDTA | 10.0 |
| Ammonium hydroxide | 4.0 |
| Water | 12.0 |

The resulting pH was 6.9 and the zinc pyrithione was successfully solubilized.

The same solubilization results are achieved when water is substituted directly from the detergent mix in the above examples.

Example 5

The five compositions set forth below further illustrate the successful solubilization of pyrithione using detergents other than those of Examples 1-5.

| | Percent | | | | |
|---|---|---|---|---|---|
| Composition No. | 1 | 2 | 3 | 4 | 5 |
| Triethanolamine Lauryl Sulfate (40% active) | 37.50 | 50.00 | — | — | 30.00 |
| Ammonium Lauryl Sulfate (28% active) | — | — | 53.57 | 71.42 | — |
| Cocamidopropyl Betaine (28% active) | — | — | — | — | 28.57 |
| Zinc pyrithione | 1.11 | 1.11 | 1.11 | 1.11 | 1.11 |
| Ethanolamine | 1.67 | 1.67 | 1.67 | 1.67 | 1.67 |
| Diethylene glycol | 3.33 | 3.33 | 3.33 | 3.33 | 3.33 |
| EDTA | 9.26 | 9.26 | 8.18 | 8.18 | 9.14 |
| Ammonium hydroxide | 4.10 | 4.10 | 3.63 | 3.63 | 4.04 |
| Water | 43.03 | 30.53 | 28.51 | 10.66 | 22.14 |

Example 6 (Comparative Example)

Example 1 was repeated six times, each time substituting one of the amines of the table below for the ethanolamine of Example 1 and the results are as shown below.

| Amine | Final Clarity |
|---|---|
| Polyethyleneimine 200 (Polymin ® G20) | Precipitate |
| QUADROL ® | " |
| EDA ® 160 | " |
| TETRONIC ® 304 | " |
| Tetraethylene pentamine (TEPA) | " |
| Polyoxyethylated TEPA | " |

In the above, the components indicated by the trademarks QUADROL ® and TETRONIC ® 304 and by EDA 160 are polyoxyalkaline block copolymers having the following generalized formula:

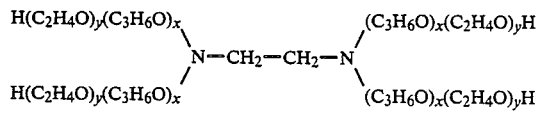

For EDA 160, x=0 and y=1, for the product sold under the trademark QUADROL ®, x is 1 and y is 0. For the product sold under the trademark TETRONIC ® 304, the value of x is such that the molecular weight of the oxypropylene groups totals about 500 to 1000 and the percentage of oxyethylene groups is about 40 percent by weight.

In the above table, polyethyleneimine 200 is a 200 molecular weight polyethyleneimine.

Polyoxyethylated TEPA has a molecular weight of about 5000.

Any system that successfully solubilizes salts of pyrithione remains of value only if it maintains the intended performance of the pyrithione. Several mechanisms of activity have been postulated to date. One mechanism, specifically antimicrobial activity, may be evaluated using a recognized serial dilution method. The method determines the "Minimum Inhibitory Concentration" (MIC) of active required to inhibit microbial growth. The method and results are set forth in Examples 7-9 below.

Examples 7-9

The test design comprises a progressive dilution of the solubilized pyrithione/shampoo system of Example 1 above, beginning with a pyrithione concentration of 10,000 micrograms per milliliter (1 percent) down to 0.078 μg/ml. The growth media for the dilutions was Mueller Hinton broth for C. Albicans and P. Aeruginosa. Agar Media 1072 was used for P. Ovale. Appropriate controls, stated below, were identically treated. All dilutions were either innoculated or streaked as appropriate with a known amount of organism. The samples were incubated and regularly observed for growth. The minimum concentration of the particular material with appropriate media which allows growth and the next higher concentration where no growth is seen bound the range where the MIC exists. The following sample code applies to all MIC test results:

1=Formulation of the Example 1 finished shampoo formulation

2=Example 1, substituting water for the detergents

3=Formulation of the Example 1 finished shampoo without pyrithione

4=The formulation of sample #3, substituting water for the Example 1 detergents

5=Formulation consisting of 70 percent of the detergents, balance water

| Sample | Minimum Inhibitory Concentration (micrograms/milliliter) |
|---|---|
| | *Candida Albicans* in Broth |
| 1 | 0.156-0.312 |
| 2 | 0.156-0.312 |
| 3 | 5.000-10.000 |
| 4 | 5.000-10.000 |
| 5 | 5.000-10.000 |
| | *Pseudomonas Aerugonosa* in Broth |
| 1 | 10.0-19.0 |
| 2 | 19.0-39.0 |

| Sample | Minimum Inhibitory Concentration (micrograms/milliliter) |
|---|---|
| 3 | 156.0–312.0 |
| 4 | 1250–2500 |
| 5 | 1250–2500 |
| *Pityrosporum Ovale* on Agar | |
| 1 | 2.5–5.0 |
| 2 | 2.5–5.0 |
| 3 | 10.0–19.0 |
| 4 | 10.0–19.0 |
| 5 | 312.0–625.0 |

These results demonstrate that pyrithione, when solubilized as taught by this invention, maintains antimicrobial activity.

What is claimed is:

1. A method for solubilizing an amount effective for the treatment of seborrhea of a metal pyrithione salt in a shampoo composition, comprising:
    (a) mixing the metal pyrithione salt with an amine having the following formula:
    $H_xN[(CH_2)_yX]_z$ wherein x is 0 to 2, y is 1 to 3, z is 1 to 3, x+z=3 and X is H, OH or COOH, until the product of (a) is clear;
    (b) mixing a cosmetically effective amount of a polycarboxylic acid selected from the group consisting of ethylenediamine tetraacetic acid, diethylene triamine pentaacetic acid, nitrilotriacetic acid, cyclohexanediamine tetraacetic acid, triethanolamine ethylenediamine tetraacetic acid and acids having the formula:

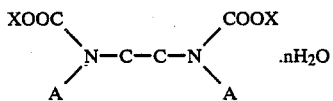

where X is H, lithium, sodium, potassium, cesium, magnesium, calcium, nickel, copper, zinc and mixtures thereof, A is H or COOX, and n is an integer or 0, with water and ammonium hydroxide,
    (c) slowly adding the product of (b) to the product of (a), and;
    (d) adding from about 10 to 70 weight percent of a surfactant selected from the group consisting of ammonium lauryl sulfate, ammonium lauryl ether sulfate, and mixtures thereof, whereby the composition has a pH of from about 4 to 7.4.

2. The method of claim 1, further including mixing an cosmetically effective amount of an alcohol selected from the group consisting of methanol, ethanol, isopropanol, butanol, propanol, diols and triols having an aliphatic chain length of 2 to 4 carbon atoms with these units repeating two to three times, ethylene oxide/propylene oxide block copolymers of molecular weight less than 1000, homopolymers of ethylene oxide or propylene oxide of molecular weight less than 1000, thiodiglycol, hexahydric alcohols, dissacharides, alkylphenol ethoxylates and mixtures thereof, with the product of (a).

3. The method of claim 1, wherein said mixture comprises about 0.1 to 20 percent by weight of said metal pyrithione, about 0.1 to 60 percent by weight amine, about 0.5 to 20 percent polycarboxylic acid, 0 to 85 percent by weight water, 0.1 to 20 percent by weight ammonium hydroxide and from about 10 to 70 weight percent surfactant, wherein the weight ratio of metal pyrithione to amine is about 1:3 to 1:1.

4. The method of claim 3, further including up to about 70 percent alcohol, wherein the weight ratio of alcohol to amine is about 2:1 to 1:1.

5. The method of claim 1, wherein the weight ratio of metal pyrithione salt to amine is about 1:3 to 1:1.

6. The method of claim 1, wherein said metal pyrithione salt is zinc pyrithione and wherein said polycarboxylic acid is ethylenediamine tetraacetic acid.

* * * * *